(12) United States Patent
Senko et al.

(10) Patent No.: US 7,297,941 B2
(45) Date of Patent: Nov. 20, 2007

(54) METHODS FOR IMPROVED DATA DEPENDENT ACQUISITION

(75) Inventors: Michael W. Senko, Sunnyvale, CA (US); Eric Hemenway, Milpitas, CA (US); Tina A. Hemenway, Milpitas, CA (US)

(73) Assignee: Thermo Finnigan LLC, San Jose, CA (US)

( * ) Notice: Subject to any disclaimer, the term of this patent is extended or adjusted under 35 U.S.C. 154(b) by 35 days.

(21) Appl. No.: 11/144,178

(22) Filed: Jun. 2, 2005

(65) Prior Publication Data

US 2006/0284067 A1    Dec. 21, 2006

(51) Int. Cl.
*B01D 59/44* (2006.01)
(52) U.S. Cl. .................. 250/282; 250/288; 702/76
(58) Field of Classification Search .......... 250/282
See application file for complete search history.

(56) References Cited

U.S. PATENT DOCUMENTS

| | | | |
|---|---|---|---|
| 5,481,476 A * | 1/1996 | Windig | 702/31 |
| 5,672,869 A * | 9/1997 | Windig et al. | 250/282 |
| 6,002,986 A | 12/1999 | Mito | |
| 2004/0181351 A1 | 9/2004 | Thompson et al. | |
| 2004/0191351 A1* | 9/2004 | Kim et al. | 425/384 |
| 2004/0251409 A1 | 12/2004 | Le Blanc | |
| 2006/0284069 A1 | 12/2006 | Le Blanc | |

OTHER PUBLICATIONS

Andreev et al., "A Universal Denoising and Peak Picking Algorithm for LC-MS Based on Matched Filtration in the Chromatographic Time Domain," Anal. Chem., vol. 75 ( No. 22), p. 6314-6326, (Nov. 15, 2003).

Kohli et al., "An Alternative Sampling Algorithm for Use in Liquid Chromatography/Tandem Mass Spectrometry Experiments," Rapid Commun. Mass Spectrom., Wiley InterScience, p. 589-596, (2005).
Wenner et al., "Factors That Affect Ion Trap Data-Dependent MS/MS in Proteomics," Amer. Soc. Mass Spectrom., Elsevier Inc., p. 150-157, (2004).

\* cited by examiner

*Primary Examiner*—Robert Kim
*Assistant Examiner*—Phillip A. Johnston
(74) *Attorney, Agent, or Firm*—Blakely Sokoloff Taylor & Zafman LLP; David E. Allred

(57) ABSTRACT

A method of analyzing data from a mass spectrometer for a data dependent acquisition is described. In an embodiment of this method, mass spectral scans are taken of a sample eluted from a liquid chromatography column. An extracted ion chromatogram (XIC) is then created for each m/z data point of the mass spectral scans and the XIC for each m/z data point are correlated to a model function, such as a monotonically increasing function, or the first half of a gaussian function, to obtain a XIC correlation value. A weighting function is then applied to the XIC correlation value to obtain a current weighted intensity. The current weighted intensity for each m/z point is used to reconstruct a weighted mass spectrum, which is then used to make a real-time decision for the data dependent acquisition. In an embodiment, the data dependent acquisition is the performance of tandem mass spectrometry.

Embodiments of the invention also describe a sample processing apparatus for the data dependent acquisition and a computer readable medium that provides instructions to the sample processing apparatus to perform the method described above.

20 Claims, 6 Drawing Sheets

METHODS FOR IMPROVED DATA DEPENDENT ACQUISITION

BACKGROUND OF THE INVENTION

1. Field of the Invention

The present invention relates to the field of data dependent acquisition in a mass spectrometer, and more particularly to the field of tandem mass spectrometry.

2. Discussion of the Related Art

Mass spectrometers are often coupled with chromatography systems in order to identify and characterize eluting species from a test sample. In such a coupled system, the eluent is ionized and a series of mass spectral scans are obtained at specified time intervals for subsequent data analysis. As the test sample may contain many species or compounds, it is often desirable to be able to automatically determine or identify species or compounds of interest as they elute and perform tandem mass spectrometry analysis to characterize them.

Tandem mass spectrometry is a mode of operation that utilizes multiple stages of mass analysis with a collision or reaction process between each stage of mass analysis. The coupling of multiple stages of mass analysis provides the ability to determine or identify species or compounds of interest by providing additional information on the fragmentation or reaction characteristics of the compound. Tandem mass spectrometry having two stages of mass analysis is typically referred to as mass spectrometry/mass spectrometry (MS/MS). In data dependent mode, the eluting sample is automatically selected for further analysis by MS/MS when the signal intensity of a mass spectral peak is above a user specified intensity. But, direct intensity based triggering is far from ideal, for several reasons. First, high baselines will cause triggering at all masses. Second, tandem mass spectra will be collected as soon as an eluting chromatographic peak exceeds the threshold value, and not at the ideal point, which is at the top of the chromatographic peak where it is at its greatest intensity. Collecting a sample for MS/MS at the beginning of the elution of the chromatographic peak produces a lower quality spectrum, due to a limited number of sample ions being combined with a high percentage of background contaminants. For ion accumulating mass spectrometers, which use automatic gain control, such as quadrupole ion traps and Fourier transform mass spectrometers, performing MS/MS at the beginning of elution also requires the largest amount of time, thus slowing analysis. Third, direct intensity based triggering results in redundant MS/MS acquisition of compounds during the entire elution time.

United States Published Patent Application US 2004/0251409 describes a method of dynamic background signal exclusion in chromatography/mass spectrometry data-dependent data acquisition to detect species eluting at a low level of concentration that elute simultaneously with a number of other major components by identifying ions having a fast rising mass signal. The ions having the fastest rising mass signal may be identified by subtracting a previously acquired mass spectrum, or an average of previously acquired mass spectra, from the current mass spectrum. The disadvantage of taking a sample of the eluted ionized species at the fastest rising mass signal is that MS/MS can often be triggered on noise spikes in the spectrum, caused by either charged droplets from the ion source or electrical noise in the detection system.

SUMMARY OF THE INVENTION

A method of analyzing data from a mass spectrometer for a data dependent acquisition is described. In an embodiment of this method, mass spectral scans are taken of a sample eluted from a liquid chromatography column. An extracted ion chromatogram (XIC) is then created for each m/z data point of the mass spectral scans and the XIC for each m/z data point are correlated to a model function, such as a monotonically increasing function, or the first half of a gaussian function, to obtain a XIC correlation value. A weighting function is then applied to the XIC correlation value to obtain a current weighted intensity. The current weighted intensity for each m/z point is used to reconstruct a weighted mass spectrum, which is then used to make a real-time decision for the data dependent acquisition. In an embodiment, the data dependent acquisition is the performance of tandem mass spectrometry.

Embodiments of the invention also describe a sample processing apparatus for the data dependent acquisition and a computer readable medium that provides instructions to the sample processing apparatus to perform the method described above.

DETAILED DESCRIPTION

In the following description numerous specific details are set forth in order to provide a thorough understanding of the present invention. One of ordinary skill in the art will understand that these specific details are for illustrative purposes only and are not intended to limit the scope of the present invention. Additionally, in other instances, well-known processing techniques and equipment have not been set forth in particular detail in order to not unnecessarily obscure the present invention.

Embodiments of the present invention describe methods of determining when to make a data dependent acquisition in real-time. In particular, the embodiments apply to the determination of when to execute tandem mass spectrometry on a precursor. In one embodiment, the data collected from a mass spectrometer is correlated to a model function and a weighting function is applied to the correlated data to obtain a reconstructed mass spectrum to make a real-time decision for a data dependent acquisition. The data dependent acquisition may be the performance of tandem mass spectrometry on a precursor ion near the apex of the chromatographic peak containing the precursor ion.

Figure 1:
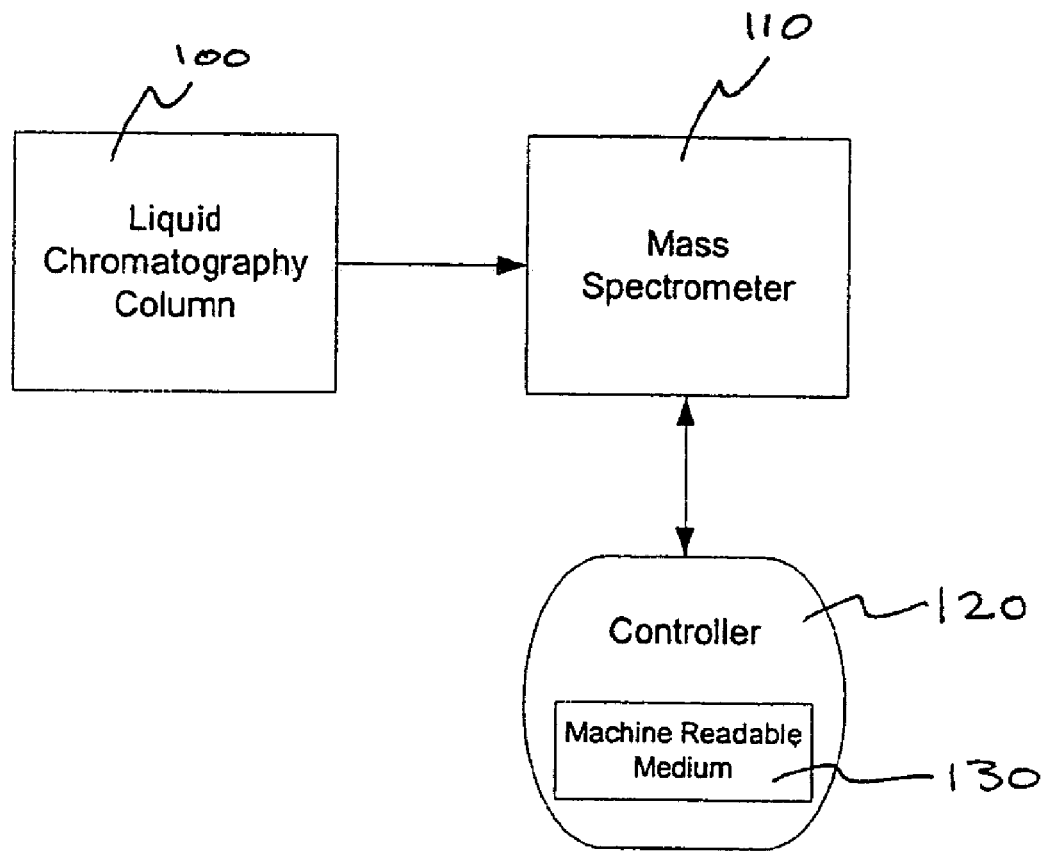
FIG. 1 is an illustration of a sample processing apparatus for data dependent acquisition.

FIG. 1 illustrates the basic components of a sample processing apparatus for data dependent acquisition that includes a liquid chromatography column 100 coupled to a mass spectrometer 110 and a system controller 120 for controlling the mass spectrometer 110 coupled to the mass spectrometer 110. The system controller 120 is coupled to a machine-readable medium 130 that has a memory storing a set of instructions to control the data dependent acquisition by the mass spectrometer. The set of instructions stored within the memory of the machine-readable medium 130 further controls all parameters of the data dependent acquisition of the mass spectrometer 110, as described in greater detail below.

In an embodiment, the method of analyzing data from a mass spectrometer for a data dependent acquisition in real-time includes first taking a series of mass spectral scans of a sample that has eluted from the liquid chromatography column 100. After eluting from the liquid chromatography column 100, the sample may be ionized by electrospray ionization to put the liquid sample into an ionized gas phase. Other ionization methods may alternately be used, such as atmospheric pressure chemical ionization, particle beam ionization, and thermospray ionization. After the sample is ionized, the ionized sample is steered into an ion trap using electrodynamic and electrostatic forces. In this embodiment, the ion trap is the mass analyzer of the mass spectrometer 110. The ionized sample is accumulated within the ion trap to the point where the ion trap contains enough of the precursor ions within the sample to obtain a mass spectrum on the contents of the ion trap at block 202 of the block diagram 200 illustrated in FIG. 2. The amount of ionized sample within the ion trap may be the same for each mass spectrum scan by using automatic gain control (AGC) (for greater description of AGC see U.S. Pat. Nos. 5,107,109 and 5,572,022). Automatic gain control is a method whereby the rate of ion flow into the trap is measured by a prescan to determine the amount of time to fill the ion trap to contain the same amount of ions before each mass spectral microscan. Several mass spectral microscans may be taken before being averaged into a single mass spectral scan. The frequency at which the average mass spectral scan is formed is very dependent on the specific instrument type and the operating mode. Typically, instruments may take one scan per second, although there are some that are capable of up to 100 scans per second. The number of microscans acquired is user selectable. A standard Thermo Finnigan ion trap scans the full mass range 5-6 times per second, with most users operating with a single microscan. The choice of the number of microscans a trade-off between speed and spectral quality. The fewer the number of scans, the faster the speed. The greater the number of scans, the higher the spectral quality.

The above embodiment describes the use of a tandem mass spectrometer with a single analyzer (known as tandem in time), the ion trap (IT). But other single stage analyzer systems capable of tandem mass spectrometry are within the scope of this invention, such as a linear ion trap (LIT), ion cyclotron resonance (ICR), orbitrap or FTMS.

The invention can also be utilized in a tandem mass spectrometer with more than one analyzer (known as tandem in space.) For example, one mass analyzer can isolate one precursor from many precursors entering a mass analyzer, after which the isolated precursor is collided with a gas within a collision cell causing fragmentation of the isolated precursor. A second mass analyzer then catalogs the fragments produced from the fragmented isolated precursor. This process is called collision-induced dissociation and is used for many experiments in proteomics. Multiple stage mass analyzers are utilized for such applications, such as a Quadrupole/oa-time-of-flight (TOF), LIT-TOF, LIT-orbitrap, Quadrupole-ICR, IT-ICR, LIT-oa-TOF, or a LIT-orbitrap mass analyzer.

Figure 3A:
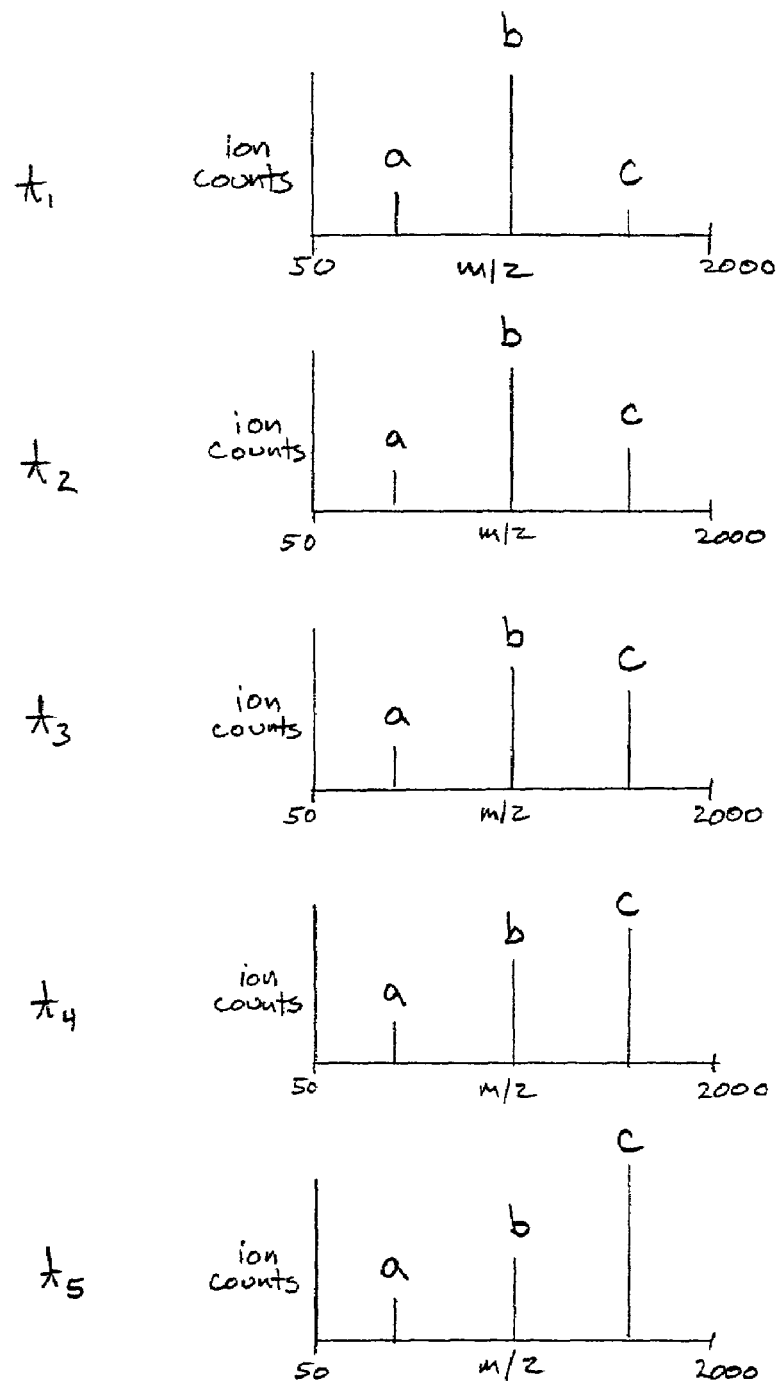
FIGS. 3A-3C illustrate the correlation method to determine when to make a data dependent acquisition.
Figure 3B:
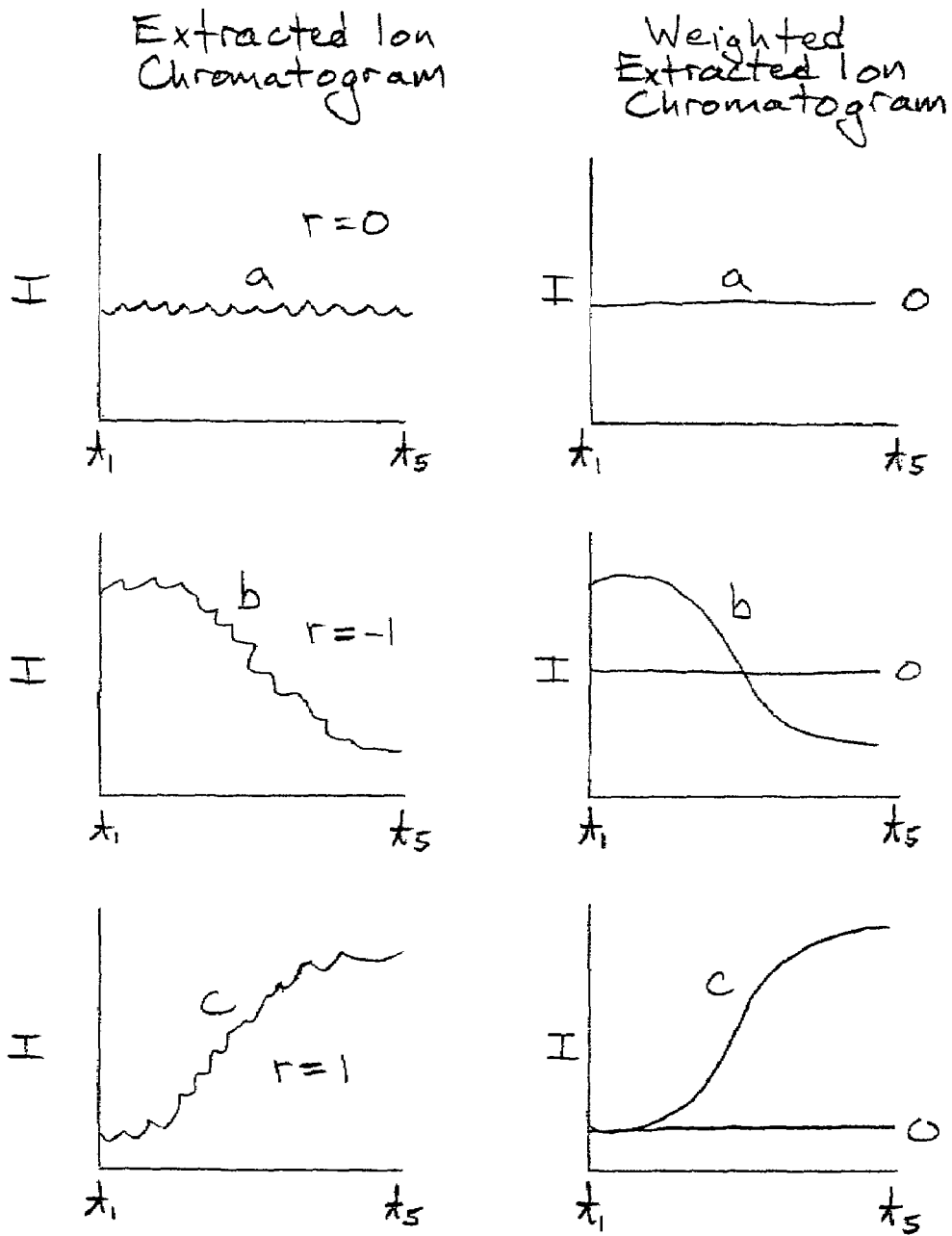

Examples of mass spectral scans are illustrated in FIG. 3A. In each of the mass spectrum scans illustrated in FIG. 3A, the ion counts are plotted on the y-axis and the m/z (mass to charge ratio) data points are plotted on the x-axis. The m/z data points are a measure of the mass (m) divided by charge (z) of each of the ions detected by the mass spectrometer of the contents of the ion trap. The m/z data points used for processing may be raw data or a copy of the raw data. Using a temporary copy of the raw data may allow for enhanced data dependent performance without actually altering the data that is returned to the data system and stored in the memory of the controller 120. Once mass spectra have been collected for a predetermined amount of time, an extracted ion chromatogram (XMC) is created for each m/z data point within the mass spectrum at block 204. The optimal duration of the predetermined amount of time over which the mass spectra are collected to create the XIC is dependent on the width of peaks eluting from the chromatograph. In one embodiment, the predetermined amount of time over which the mass spectra are collected is between one-half chromatographic peak widths and three chromatographic peak-widths, as measured at half maximum height of the chromatographic peaks. The predetermined amount of time can either be fixed or can be automatically adjusted based upon observed chromatographic peak widths. To minimize processing overhead (in particular time), two or more m/z points, or m/z points falling within defined ranges, can be combined before creating each XIC. FIG. 3A illustrates an example of five mass spectra taken at different times ($t_1$ through $t_5$), which for purposes of explanation contain only three m/z data points a, b, and c. It is to be understood that the number of mass spectra used to form the extracted ion chromatograms and the number of m/z data points within the mass spectra may vary. The number of mass spectra used to form the extracted ion chromatograms may be within the approximate range of 3 and 20, and the number of m/z data points may be in the approximate range of 5,000 and 1,000,000 in a mass spectrum. The wide range of m/z data points that may be collected is due to the variation among different instruments. For example, an ion trap instrument may acquire approximately 15,000 data points and a Fourier transform instrument may acquire approximately 1,000,000 data points. FIG. 3B illustrates the extracted ion chromatograms created for each of the m/z data points (a, b, and c) within the mass spectra of FIG. 3A.

Figure 2:
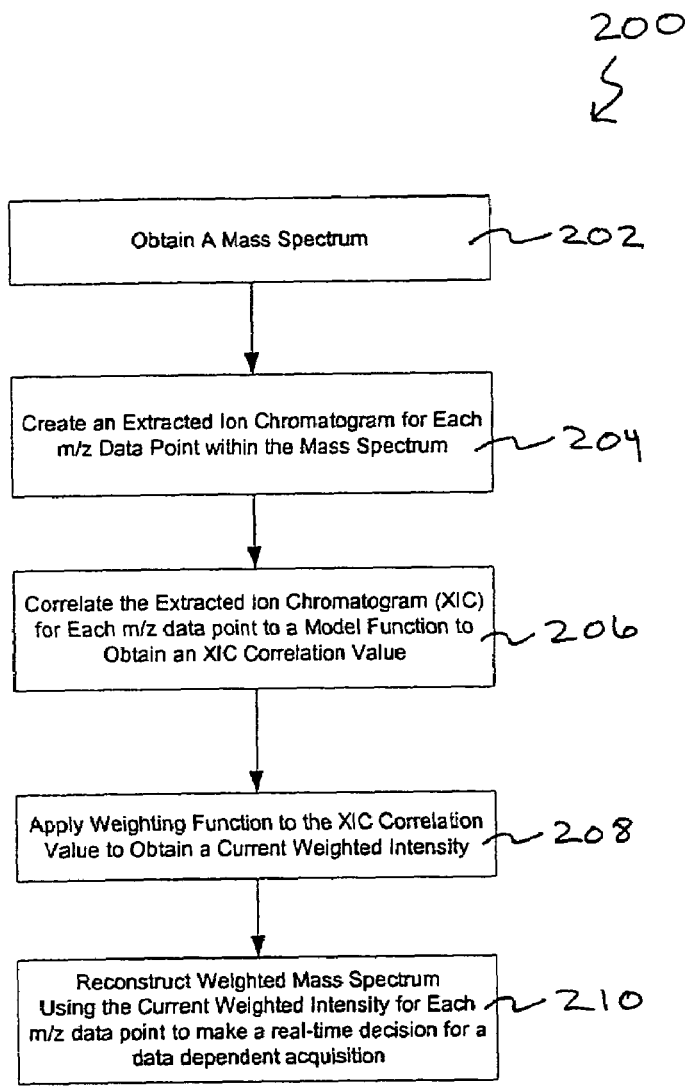
FIG. 2 is a block diagram of the correlation method to determine when to make a data dependent acquisition.

The extracted ion chromatogram for each of the m/z data points is then correlated to a model function, in one aspect of the invention a monotonically increasing function, or a gaussian function, to obtain a XIC correlation value at block 206 of FIG. 2. The model function is a function (a set of time vs. intensity pairs) that matches the expected elution profile of an analyte from a chromatograph. The gaussian function works well for correlation because the chromatographic peaks often have a gaussian shape, but any montonically increasing function may be used. Other monotonically increasing functions that may be used include, but are not limited to, a Lorentzian function or a linear function. The XIC correlation value r for the m/z data point c at time point $t_5$ is approximately +1 because the XIC for c matches the front half of a gaussian peak. The correlation value r is a measure of how closely the XIC correlates to the first half of a gaussian function or a monotonically increasing function. The XIC correlation value may be any value between −1 and +1. A weighting function is then applied to the XIC correlation value to obtain a current weighted intensity at block 208 of FIG. 2. FIG. 3B illustrates examples of the weighted extracted ion chromatograms for the m/z data points a, b, and c. Therefore, in the example illustrated in FIG. 3B, the current weighted intensity for m/z data point a is approximately 0 because the XIC for a is neither increasing nor decreasing. The current weighted intensity for the m/z data point b is negative because the XIC for b is decreasing.

The weighting function provides a scaling factor to the raw intensities to reflect how well the XIC represents the expected elution profile. The weighting function may be the product of the XIC correlation value and the most recent time point, the product of a square of the XIC correlation value and the most recent time point, or the most recent time point raised to the power of XIC correlation value. The weighting function serves to emphasize the mass spectral peaks that occur at the actual apex of the chromatographic peak and to also prevent triggering on a tail of a chromatographic peak. This is because once the apex of a chromatographic peak has been passed, the XIC correlation value will be negative. The weighting function also serves to improve the signal-to-noise in real-time because when the XIC correlation values are near zero, then it is likely that signal is primarily noise The low intensity peaks may be picked out by this process even when eluting at the same time as a peak of much higher intensity or as a shoulder of another peak. With this method, it is also possible to differentiate eluting peaks from one another when there are many overlapping peaks eluting at the same time and to identify peaks that are much smaller in comparison to other peaks eluting at the same time. This is because the intensity of each m/z data point is independently monitored over time, so even a peak hidden beneath another peak or within noise may be reliably identified.

In an embodiment, a threshold value may be applied to the weighted intensity values to eliminate values below a certain threshold value. For example, the threshold value may be used to de-emphasize a very strong background peak that is not eluting (i.e. it is at a constant level) but may occasionally have a weak (approximately 0.1) correlation. The weighted intensity for this very strong background peak may still result in a strong signal. Restricting the correlation value to something such as >0.5 places a stronger emphasis on the XIC elution profile than on the very strong background peak. Additionally, a threshold value may be used because it is mathematically easier and faster to be able to disregard all of the values below the threshold value.

Although the above indicates that the correlation coefficient is the technique used to compare the similarity between the XIC data points and the model function, to provide a value that represents how similar they are, the use of the correlation technique is only one aspect of the invention. Other techniques or methods of determining how well the XIC data points fit the model function may serve to accomplish this aim. In this application, the term "correlation" is intended to cover these alternative techniques.

Figure 3C:
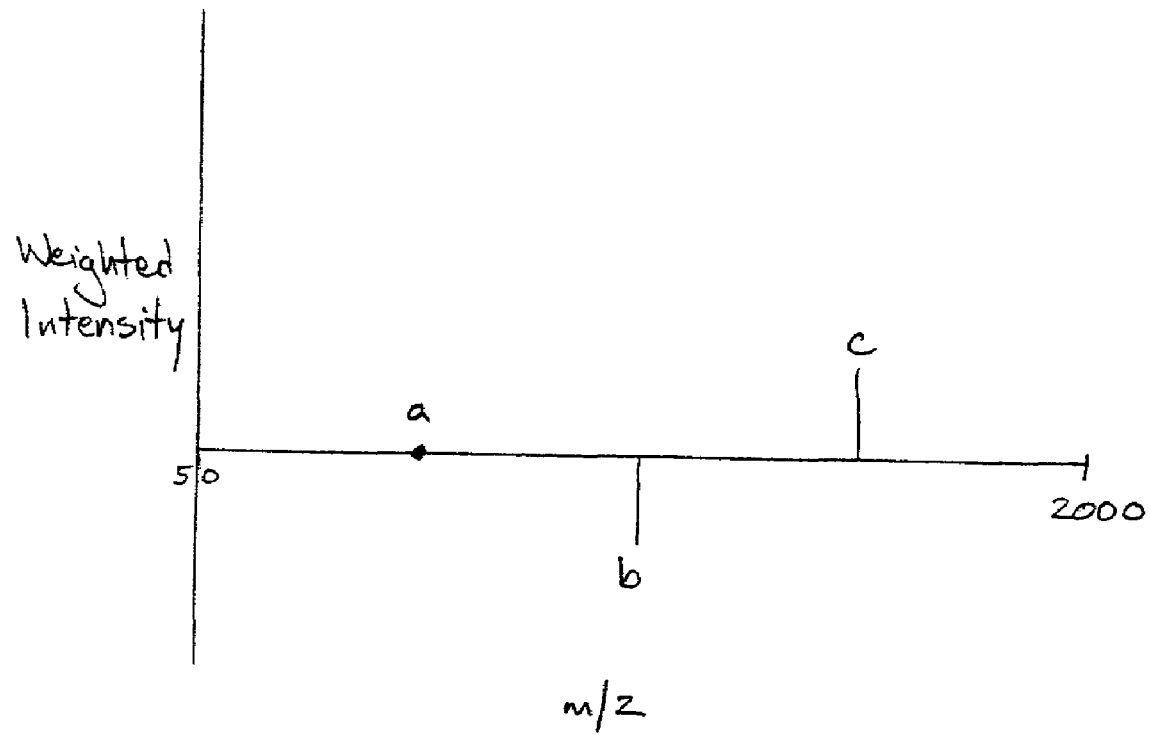

At block 210 of FIG. 2, a weighted mass spectrum is reconstructed using the current weighted intensities for each m/z data point to make a real-time decision for the data dependent acquisition. An example of a weighted mass spectrum is illustrated in FIG. 3C based on XEC correlation values of the extracted ion chromatograms of FIG. 3B. The current weighted intensities for each of the different m/z data points within the reconstructed weighted mass spectrum give an indication of whether the precursor ions from which the m/z data points are derived are increasing, constant, or decreasing in intensity and therefore whether a chromatographic elution peak of the precursor ions exists and whether it is approaching or has already been passed. Whether the chromatographic elution peak is approaching or has already been passed is valuable information for determining when to make a data dependent acquisition. The data dependent acquisition may be, for example, the performance of tandem mass spectrometry, the collection of a particular isolated compound eluted from the liquid chromatography column, a diversion to a nuclear magnetic resonance (NMR) analysis, or the spotting of the compound onto a matrix assisted laser desorption and ionization (MALDI) plate.

Figure 4:
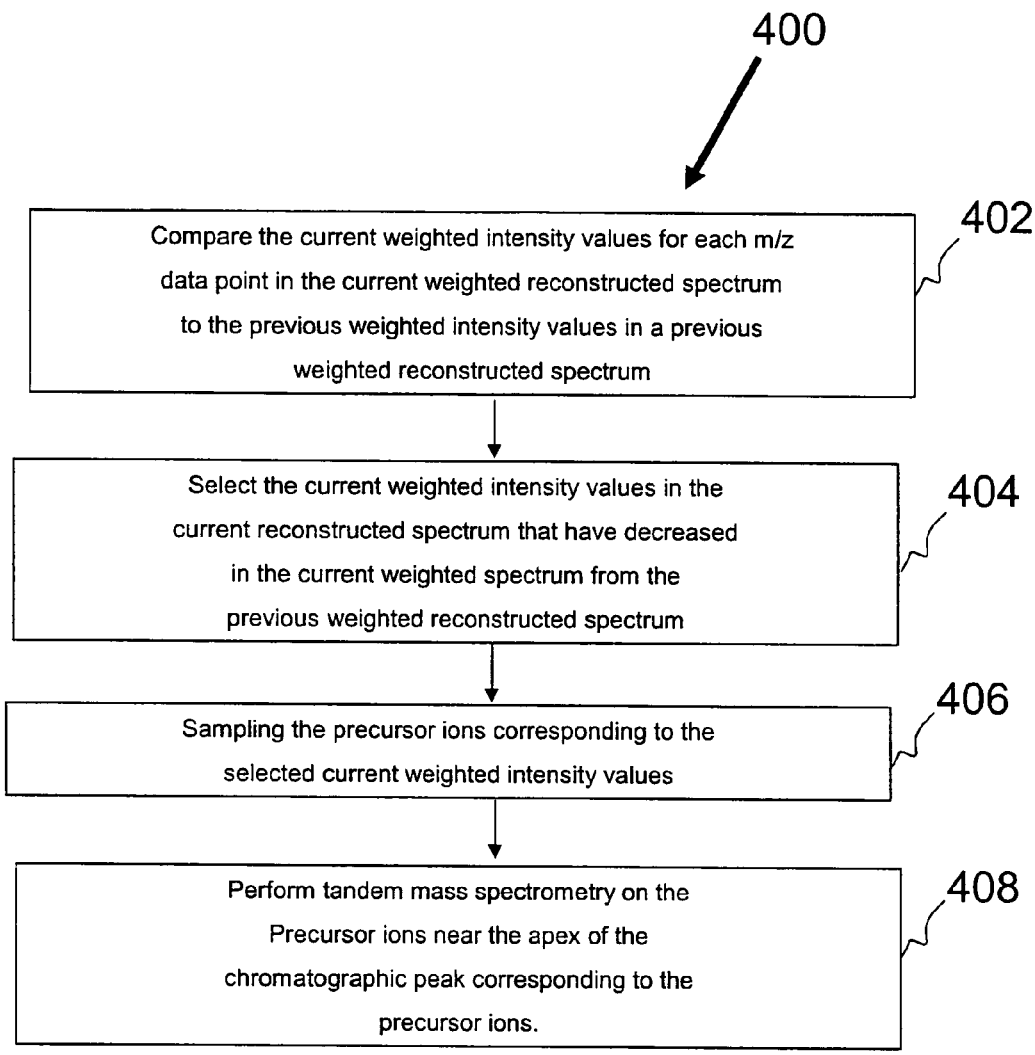
FIG. 4 is a block diagram of methods of selecting mass spectral m/z data points near the apex of the chromatographic peak for tandem mass spectrometry.

FIG. 4 is a flow chart 400 illustrating an embodiment of a process of performing the data dependent acquisition near the apex of a chromatographic peak. In this process, the method of analyzing data from a mass spectrometer for data dependent acquisition is expanded upon after reconstructing the weighted mass spectrum. At block 402, the weighted intensity for each m/z data point in the current weighted mass spectrum is compared to the weighted intensity for each m/z data point in a previous weighted mass spectrum.

At block 404, an m/z data point (precursor ion) is then selected if its weighted intensity has decreased in the current weighted mass spectrum from the previous weighted mass spectrum. In the embodiment where tandem mass spectrometry is performed, the precursor ions corresponding to the selected weighted intensities is sampled at block 406 and tandem mass spectrometry is performed on the precursor ion near the apex of the chromatographic peak containing the precursor ion at block 408.

In the embodiment where the data dependent acquisition is the performance of tandem mass spectrometry, it is valuable to perform tandem mass spectrometry on a precursor ion near the apex of the chromatographic peak containing the precursor ion. In tandem mass spectrometry, precursor ions are further fragmented by collision or reaction within a separate chamber or within the ion trap itself. The further fragmentation of the precursor ions on which mass spectra are obtained creates more information for the characterization or identification of compounds eluting from the chromatographic column. The apex of the chromatographic peak is an advantageous place to collect the precursor ions for tandem mass spectrometry because the flux of ions into the ion trap near the apex of the peak is at its greatest. Therefore, the ion trap may be quickly filled to capacity with the ions of interest, resulting in the faster production of mass spectra and reduced signal to noise ratios. The signal to noise ratio may be enhanced because the time to fill the ion trap to capacity is minimized so that any contaminants, if present within the sample, may be present in insignificant quantities. Additionally, filling the ion trap to capacity is valuable because it provides more precursor ions within the resulting mass spectrum.

In an embodiment, an added enhancement to the method would be the monitoring of the overall signal intensity (or total ion current). If the source happened to be unstable for a second or two, the intensity of all of the peaks would be lower, which would trigger the system to perform MS/MS on all precursors that were previously above threshold. If the overall signal intensity dropped significantly, indicating a loss of source stability, all unstable scans could be excluded from the data dependent decision making process.

It is to be appreciated that the disclosed specific embodiments are only meant to be illustrative of the present invention and one of ordinary skill in the art will appreciate the ability to substitute features or to eliminate disclosed features. As such, the scope of the Applicant's invention is to be measured by the appended claims that follow.

We claim:

1. A method of analyzing data from a mass spectrometer for a data dependent acquisition, comprising:
   obtaining a mass spectrum of a sample;
   creating an extracted ion chromatogram (XIC) for each m/z data point of the mass spectrum;

correlating the XIC for each m/z data point of the mass spectrum scans to a model function corresponding substantially only to a front half of a peak to obtain a XIC correlation value;

applying a weighting function to the XIC correlation value for each m/z data point to obtain a current weighted intensity; and reconstructing a weighted mass spectrum using the current weighted intensity for each m/z data point to make a real-time decision of when to make the data dependent acquisition such that the acquisition is made at a time corresponding to an apex of each m/z data point.

2. The method of claim 1, wherein the model function is a monotonically increasing function.

3. The method of claim 1, wherein the model function is a gaussian function.

4. The method of claim 1, wherein one or more of the m/z data points are combined before creating the extracted ion chromatogram.

5. The method of claim 1, wherein the sample has an elution chromatogram with a chromatographic peak width, and the extracted ion chromatogram (XIC) is formed of mass spectra collected for a predetermined amount of time between one half and three times the width of a chromatographic peak width.

6. The method of claim 5, wherein the peak width is measured at half maximum height.

7. The method of claim 1, wherein the data dependent acquisition comprises performing tandem mass spectrometry on a precursor ion near an apex of a chromatographic peak containing the precursor ion.

8. The method of claim 7, wherein performing tandem mass spectrometry on the precursor ion near the apex of the chromatographic peak containing the precursor ion comprises: comparing the current weighted intensity value for each m/z data point in the current weighted reconstructed mass spectrum to a previous weighted intensity value for each m/z data point in a previous weighted reconstructed mass spectrum;

selecting the current weighted intensities in the current mass spectrum that have decreased in the current weighted mass spectrum from the previous weighted mass spectrum; and sampling the precursor ions corresponding to selected current weighted intensities to perform tandem mass spectrometry.

9. The method of claim 1, wherein the sample is subjected to a liquid chromatographic process prior to taking mass spectrum scans of the sample.

10. The method of claim 1, wherein the weighting function comprises a product of the XIC correlation value and the m/z data point intensity.

11. The method of claim 1, wherein the weighting function comprises a product of a square of the XIC correlation value and the m/z data point intensity.

12. The method of claim 1, wherein the weighting function comprises the m/z data point intensity raised to the power of the XIC correlation value.

13. The method of claim 1, further comprising selecting the XIC correlation values above a threshold value before applying the weighting function to the correlated XIC values to obtain the weighted intensity for each m/z data point.

14. The method of claim 1, wherein the method of data dependent acquisition is performed on raw data in real time.

15. A sample processing apparatus for data dependent acquisition, comprising:

a mass spectrometer;

a system controller for controlling the mass spectrometer;

a machine-readable medium coupled to the system controller, the machine-readable medium has a memory that stores a set of instructions that controls data dependent acquisition by the mass spectrometer; wherein:

the set of instructions further controls all parameters of the data dependent acquisition of the mass spectrometer by obtaining a mass spectrum of a sample, monitoring each m/z data point or range of m/z data points independently over time, creating an extracted ion chromatogram (XIC) for each m/z data point or range of m/z data points of the mass spectrum, correlating the XIC for each m/z data point or range of m/z data points of the mass spectrum scans to a model function corresponding to substantially only a front half of a peak to obtain a XIC correlation value, applying a weighting function to the XIC correlation value for each m/z data point or range of m/z data points to obtain a current weighted intensity;

reconstructing a weighted mass spectrum using the current weighted intensity for each m/z data point, wherein the weighting function emphasizes mass spectral peaks that occur at apexes of chromatographic peaks; and making real-time decisions of when to make the data dependent acquisition based on the mass spectral peaks.

16. The sample processing apparatus for data dependent acquisition of claim 15, further comprising a liquid chromatography column to provide the sample for analysis by the mass spectrometer.

17. The sample processing apparatus for data dependent acquisition of claim 15, wherein the data dependent acquisition comprises performing tandem mass spectrometry on a precursor ion near an apex of a chromatographic peak containing the precursor ion.

18. The apparatus of claim 15, wherein the set of instructions further controls all parameters of the data dependent acquisition of the mass spectrometer by performing tandem mass spectrometry on the precursor ion near the apex of the m/z peak corresponding to the precursor ion by comparing the current weighted intensity for each m/z data point or range of m/z data points in the current weighted reconstructed mass spectrum to the previous weighted intensity for each m/z data point or range of m/z data points in a previous weighted reconstructed mass spectrum;

selecting the current weighted intensity values in the current mass spectrum that have decreased in the current reconstructed weighted mass spectrum from the previous weighted reconstructed mass spectrum; and sampling the precursor ions corresponding to selected current weighted intensities to perform tandem mass spectrometry.

19. A computer readable medium that provides instructions, which when executed on a processor, causes the processor to perform a method of controlling a mass spectrometer comprising:

obtaining a mass spectrum of a sample;

creating an extracted ion chromatogram (XIC) for each m/z data point or range of m/z data points of the mass spectrum;

correlating the XIC for each m/z data point or range of m/z data points of the mass spectrum scans to a model function corresponding to substantially only a front half of a peak to obtain a XIC correlation value applying a weighting function to the XIC correlation value for each m/z data point or range of m/z data points to obtain a current weighted intensity;

reconstructing a weighted mass spectrum using the current weighted intensity for each m/z data point or range of m/z data points in order to make a real-time decision of when to trigger the data dependent acquisition; and triggering at a time corresponding to an apex of each m/z data point or range of m/z data points.

20. The computer readable medium of claim 19, wherein the data dependent acquisition comprises performing tandem mass spectrometry on a precursor ion near the apex of a chromatographic peak representing the m/z data point or range of m/z data points containing the precursor ion.

* * * * *